(12) United States Patent
Bayne et al.

(10) Patent No.: US 7,417,122 B2
(45) Date of Patent: Aug. 26, 2008

(54) MAMMALIAN GALANIN RECEPTORS

(75) Inventors: Marvin Bayne, Westfield, NJ (US);
Tanaz Hashemi, Kenilworth, NJ (US);
Chaogang He, Edison, NJ (US); Suke Wang, Edison, NJ (US)

(73) Assignee: Schering Corporation, Kenilworth, NJ (US)

( * ) Notice: Subject to any disclaimer, the term of this patent is extended or adjusted under 35 U.S.C. 154(b) by 47 days.

(21) Appl. No.: 11/768,449

(22) Filed: Jun. 26, 2007

(65) Prior Publication Data

US 2007/0255044 A1   Nov. 1, 2007

Related U.S. Application Data

(60) Continuation of application No. 10/946,767, filed on Sep. 22, 2004, now Pat. No. 7,250,163, which is a continuation of application No. 10/779,021, filed on Feb. 13, 2004, now abandoned, which is a division of application No. 08/916,247, filed on Aug. 22, 1997, now Pat. No. 6,693,182.

(51) Int. Cl.
*C07K 14/00* (2006.01)

(52) U.S. Cl. ...................................... 530/350

(58) Field of Classification Search ........................ None
See application file for complete search history.

(56) References Cited

U.S. PATENT DOCUMENTS 6,329,197 B2   12/2001   Bard et al.
6,693,182 B1   2/2004   Bayne et al.

FOREIGN PATENT DOCUMENTS

EP           0711830        5/1996
WO        WO 95/22608       8/1995

OTHER PUBLICATIONS

Altschul et al., Journal of Molecular Biology 215:403-410 (1990).
Boswell et al., Computational Molecular Biology, Sources and Methods for Sequence Analysis, Ed. A. M. Lesk., Oxford U. Press, Oxford, pp. 161-178 (1988).
Burgevin et al., Journal of Molecular Neuroscience 6:33-41 (1995).
Habert-Ortoli et al., Proc. Natl. Acad. Sci., USA 91:9780-9783 (1994).
Howard et al., FEBS Letters 405:285-290 (1997).
Lagny-Pourmir et al., Endocrinology 124:2635-2641 (1989).
Parker et al., Molecular Brain Research 34:179-189 (1995).
Rieger et al., Glossary of Genetics and Cytogenetics, Classical and Molecular 5th Ed., Springer-Verlag, Berlin, pp. 16-17 (1991).
Smith et al, The Journal of Biological Chemistry 272:24612-24616 (1997).
Wang et al., Molecular Pharmacology 52:337-343 (1997).
Wang et al., FEBS Letters 411:225-230 (1997).
Williams et al., Science 196:328-330 (1977).
Stelbay, J. Immunol. 88:434-442 (1962).
Branchek et al., Annals N.Y. Acad. Sci. 863:94-107 (1988).
Branchek et al., Trends Pharm Sci. 21:109-117 (2000).

*Primary Examiner*—Bruce R. Campell
*Assistant Examiner*—Nicole Kinsey White

(57) ABSTRACT

The present invention provides isolated mammalian GalR3 receptors, isolated or recombinant nucleic acids and recombinant vectors encoding the same, host cells comprising the nucleic acids and vectors, and methods for making the receptors using the host cells. This invention further provides antibodies and antigen binding fragments thereof which specifically bind to the receptors and are useful for treating medical conditions caused or mediated by galanin. Also provided are screening methods for identifying specific agonists and antagonists of the mammalian GalR3 receptors.

20 Claims, 2 Drawing Sheets

MAMMALIAN GALANIN RECEPTORS

This application is a continuation of U.S. patent application Ser. No. 10/946,767, filed Sep. 22, 2004, now U.S. Pat. No. 7,250,163; which is a continuation of U.S. patent application Ser. No. 10/779,021, filed Feb. 13, 2004, now abandoned; which is a divisional of U.S. patent application Ser. No. 08/916,247, filed Aug. 22, 1997, now U.S. Pat. No. 6,693,182; each of which is herein incorporated by reference in its entirety.

TECHNICAL FIELD

The present invention relates to mammalian galanin receptors. More particularly, it relates to rat and human galanin receptors, isolated nucleic acids and recombinant vectors encoding the receptors, methods for making the receptors, fragments or fusion proteins thereof using recombinant DNA methodology or chemical synthesis, and to methods for using the receptors in screening systems to identify inhibitors for the treatment of various diseases. This invention further relates to antibodies, both polyclonal and monoclonal, which specifically bind to the galanin receptors or to anti-idiotypic antibodies against them, and to fragments and fusion proteins thereof.

BACKGROUND OF THE INVENTION

Galanin is a polypeptide found in the central and peripheral nervous systems which regulates multiple processes such as endocrine and exocrine pancreatic secretions, intestinal motility, and modulation of behavioral, cognitive, and sensory functions such as feeding, learning, memory and nociception. See, e.g., Merchenthaler et al., *Prog. Neurobiol.* 40:711-769 (1993), and Hökfelt et al. in *Galanin: A New Multifunctional Peptide in the Neuro-Endocrine System*, Wenner-Gren International Symposium Series, 1991, Vol. 58, MacMillan, Cambridge, U.K. Because of its wide distribution and multiple activities, Galanin is believed to be involved in a number of medical conditions, including obesity, Alzheimer's disease, nociception, dementia, eating disorders, diabetes, dislipoproteinemia, developmental disorders of the neural systems, disorders of the digestive systems growth disorders, sexual and reproductive dysfunctions, stomach ulcers, sleep disorders, and regeneration of injured neuronal systems.

The physiological effects of galanin are mediated by specific receptors in target tissues. One such receptor from insulin-secreting cells has been described by Lagny-Pourmir et al. [*Endocrinology* 124:2635-2641 (1989)]. Human galanin receptors have been cloned by Habert-Ortoli et al. [*Proc. Natl. Acad. Sci. USA* 91:9780-9783 (1994)], Hinuma et al. [European Patent Application Publication EP 0 711 830 A2] and Amiranoff et al [International Patent Application Publication No. WO 95/22608].

In view of the important role of galanin in many physiological processes and medical conditions, there is a need for materials and methods for identifying selective agonists and antagonists of galanin.

SUMMARY OF THE INVENTION

The present invention fills the foregoing need by providing such materials and methods. More particularly, this invention provides novel mammalian galanin receptors, isolated or recombinant nucleic acids encoding the receptors, and recombinant vectors and host cells comprising such nucleic acids.

The isolated or recombinant nucleic acids are selected from the group consisting of:

(a) a nucleic acid encoding a mammalian galanin receptor comprising an amino acid sequence defined by SEQ ID NO: 2 or SEQ ID NO: 4, or a subsequence thereof;

(b) a nucleic acid that hybridizes under moderately stringent conditions to the nucleic acid of (a) and encodes a polypeptide that (i) binds galanin and (ii) is at least 80% identical to a receptor encoded by the nucleic acid of (a); and (c) a nucleic acid that, due to the degeneracy of the genetic code, encodes a mammalian galanin receptor encoded by a nucleic acid of (a) or (b).

This invention further provides methods for making the galanin receptors comprising culturing a host cell comprising a nucleic acid encoding a mammalian galanin receptor comprising an amino acid sequence defined by SEQ ID NO: 2 or SEQ ID NO: 4, or a subsequence thereof, under conditions in which the nucleic acid is expressed. In some embodiments, the method further comprises isolation of the receptor from the culture.

This invention also provides polypeptides comprising a fragment of a mammalian galanin receptor having an amino acid sequence corresponding to the sequence of at least about 8 contiguous residues of the complete receptor sequence. Preferably, the polypeptides comprise at least about 12, more preferably at least about 20, and most preferably at least about 30 such residues.

Still further, this invention provides fusion proteins comprising a mammalian galanin receptor or a polypeptide therefrom covalently linked to a fusion partner.

The present invention also provides antibodies, both polyclonal and monoclonal, that specifically bind to one or more of the galanin receptors or to polypeptides therefrom, and anti-idiotypic antibodies, both monoclonal and polyclonal, which specifically bind to the foregoing antibodies.

This invention further provides a method for producing a mammalian galanin receptor comprising culturing a host cell comprising a nucleic acid encoding a mammalian galanin receptor comprising an amino acid sequence defined by SEQ ID NO: 2 or SEQ ID NO: 4, or a subsequence thereof under conditions in which the nucleic acid is expressed. In one embodiment the receptor is isolated from the culture.

This invention still further provides a method for treating galanin-mediated medical conditions comprising administering to a mammal afflicted with a medical condition caused or mediated by galanin, an effective amount of an antibody, or an antigen-binding fragment thereof, that specifically binds to a mammalian galanin receptor having an amino acid sequence defined by SEQ ID NO: 4, or a subsequence thereof, and pharmaceutical compositions comprising one or more of such antibodies or fragments and a pharmaceutically acceptable carrier. Preferably, the mammal is a human being.

The present invention also provides a method for identifying a galanin agonist or antagonist comprising:

(a) contacting a mammalian galanin receptor having an amino acid sequence defined by SEQ ID NO: 2 or SEQ ID NO: 4, or a subsequence thereof in the presence of a known amount of labeled galanin with a sample to be tested for the presence of a galanin agonist or antagonist; and (b) measuring the amount of labeled galanin specifically bound to the receptor;

whereby a galanin agonist or antagonist in the sample is identified by measuring substantially reduced binding of the labeled galanin to the galanin receptor, compared to what would be measured in the absence of such agonist or antagonist.

In a preferred embodiment, membranes isolated from mammalian cells comprising a nucleic acid encoding the galanin receptor are used as the source of the receptor.

BRIEF DESCRIPTION OF THE FIGURES

The present invention can be more readily understood by reference to the following Description and Examples, and to the accompanying Figures, in which.

DESCRIPTION OF THE INVENTION

Figure 1:
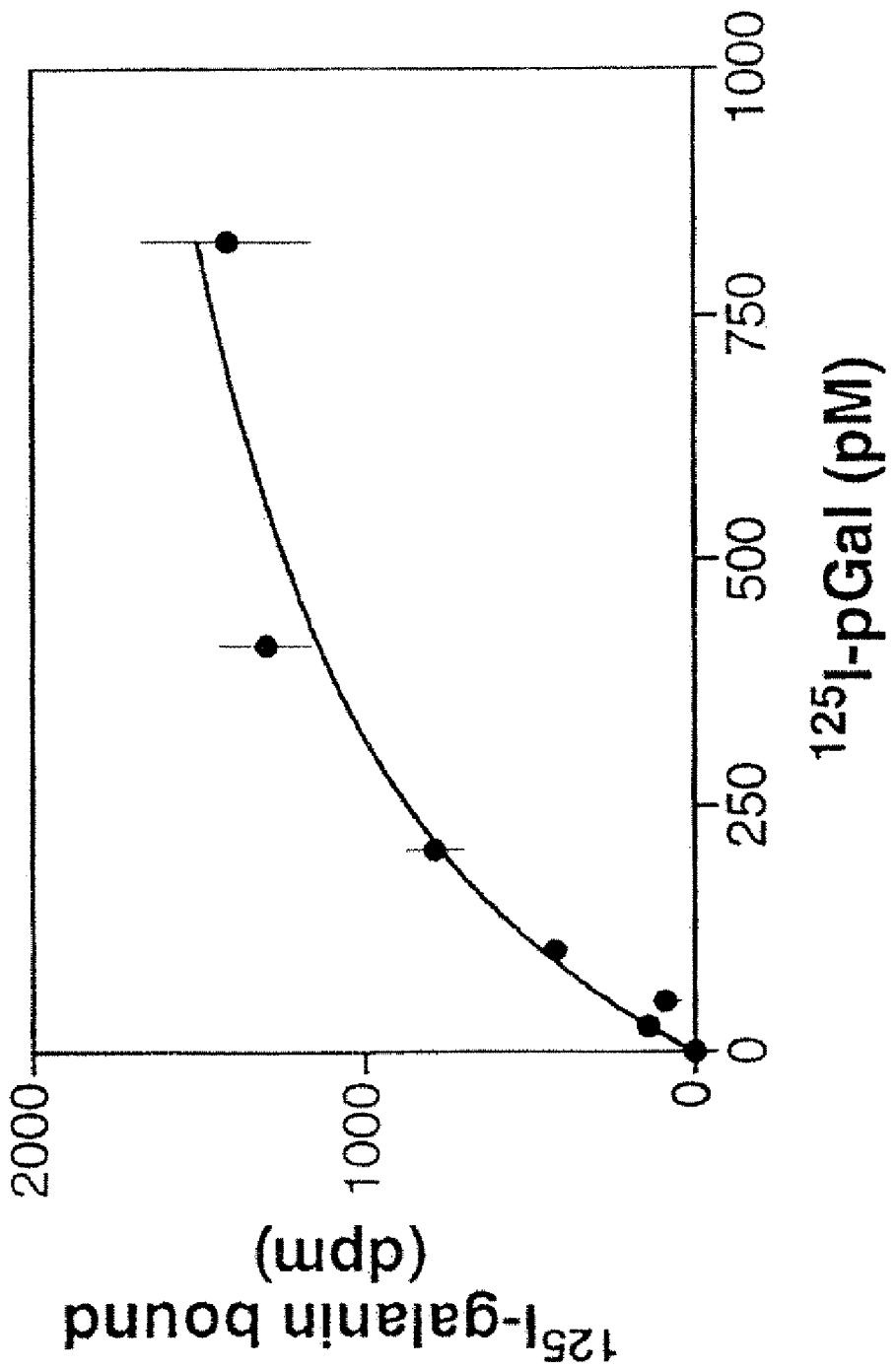
FIG. 1 is a graphical representation of the specific binding of $^{125}$I-galanin to cellular receptors, showing bound radioactivity as a function of ligand concentration.

All references cited herein are hereby incorporated herein in their entirety by reference.

As used herein, the term "ligand" is defined to mean any molecule capable of specifically binding to the mammalian galanin receptors of the invention. Thus galanin itself is a ligand, as are agonists and antagonists that may compete with galanin for specific binding to the receptors.

Galanin Receptor Characterization

As has been noted above, others had identified galanin receptors from various species and tissues prior to the present invention. Thus, there appears to be a family of galanin receptor subtypes. The human receptor cloned by Habert-Ortoli et al., supra, was the first and hence has been called the type 1 galanin receptor (GalR1). Homologous GalR1 receptors have been cloned from rat Rin14B insulinoma cells [Parker et al., Mol. Brain Res. 34:179-189 (1995)] and from rat brain [Burgevin et. al., J. Mol. Neurosci. 6:33-41 (1995)].

More recently a second galanin receptor subtype, type 2 (GalR2), has been described in rat by Howard et al. [FEBS Lett. 405:285-290 (1997) and by Wang et al [Mol. Pharmacol. Vol 52:1 (1997) (in press)]. Because of the previously known existence of type 1 and type 2 galanin receptors, the novel galanin receptors of this invention may be referred to as type 3 galanin receptors (GalR3).

The nucleotide sequence of the complete open reading frame and the corresponding amino acid sequence of rat GalR3 receptor cDNA are defined in the Sequence Listing by SEQ ID NO: 1 and SEQ ID NO: 2, respectively. The nucleotide sequence of the complete open reading frame and the corresponding amino acid sequence of the human GalR3 receptor are defined in the Sequence Listing by SEQ ID NO: 3 and SEQ ID NO: 4, respectively.

In comparing the complete rat and human EDNA sequences, it has been found that the human sequence is longer, and that a region encoded by bases 169 to 1275 (amino acid residues 61-424) of the complete human sequence is highly homologous to the rat sequence. The human GalR3 receptor sequence may thus be regarded as having two forms—a "long" form encompassing the entire sequence defined by SEQ ID NO: 4, and a "short" form encompassing the region encoded by bases 169 to 1275 of SEQ ID NO: 3.

The long form occurs naturally, as the start and stop codons were identified from human brain cDNA that was reverse-transcribed from natural transcripts. The short form may result from the long form by a modifying mechanism, e.g., from an alternative splicing of the transcript or from an independent transcript generated at a separate genomic locus, but whether that is true or not is irrelevant to this invention.

As used herein, the phrase an isolated or recombinant receptor comprising an amino acid sequence "defined by SEQ ID NO: 4, or a subsequence thereof" is thus defined to include both "short" and "long" forms of the human GalR3 receptor.

The present invention also encompasses fragments, analogs and physical variants of the receptors. As used herein, the term "polypeptide" or "peptide" means a fragment or segment, e.g., of a mammalian galanin receptor having an amino acid sequence defined by SEQ ID NO: 2 or 4 which comprises a subsequence of the complete amino acid sequence of the receptor containing at least about 8, preferably at least about 12, more preferably at least about 20, and most preferably at least about 30 or more contiguous amino acid residues, up to and including the total number of residues in the complete receptor.

The polypeptides of the invention can comprise any part of the complete sequence of such a receptor. Thus, although they could be produced by proteolytic cleavage of an intact receptor, they can also be made by chemical synthesis or by the application of recombinant DNA technology and are not limited to polypeptides delineated by proteolytic cleavage sites. The polypeptides, either alone or cross-linked or conjugated to a carrier molecule to render them more immunogenic, are useful as antigens to elicit the production of antibodies. The antibodies can be used, e.g., in immunoassays of the intact receptors, for immunoaffinity purification, etc.

The term "analog(s)" means a mammalian galanin receptor of the invention which has been modified by deletion, addition, modification or substitution of one or more amino acid residues in the wild-type receptor. It encompasses allelic and polymorphic variants, and also muteins and fusion proteins which comprise all or a significant part of such a mammalian galanin receptor, e.g., covalently linked via a side-chain group or terminal residue to a different protein, polypeptide or moiety (fusion partner).

Some amino acid substitutions are preferably "conservative", with residues replaced with physicochemically similar residues, such as Gly/Ala, Asp/Glu, Val/Ile/Leu, Lys/Arg, Asn/Gln and Phe/Trp/Tyr. Analogs having such conservative substitutions typically retain substantial galanin binding activity. Other analogs, which have non-conservative substitutions such as Asn/Glu, Val/Tyr and His/Glu, may substantially lack such activity. Nevertheless, such analogs are useful because they can be used as antigens to elicit production of antibodies in an immunologically competent host. Because these analogs retain many of the epitopes (antigenic determinants) of the wild-type receptors from which they are derived, many antibodies produced against them can also bind to the active-conformation or denatured wild-type receptors. Accordingly, such antibodies can also be used, e.g., for the immunopurification or immunoassay of the wild-type receptors.

Some analogs are truncated variants in which residues have been successively deleted from the amino- and/or carboxyl-termini while substantially retaining the characteristic ligand binding activity.

Modifications of amino acid residues may include but are not limited to aliphatic esters or amides of the carboxyl terminus or of residues containing carboxyl side chains, O-acyl derivatives of hydroxyl group-containing residues, and N-acyl derivatives of the aminoterminal amino acid or aminogroup containing residues, e.g., lysine or arginine.

Other analogs are mammalian galanin receptors containing modifications, such as incorporation of unnatural amino acid residues, or phosphorylated amino acid residues such as phosphotyrosine, phosphoserine or phosphothreonine residues. Other potential modifications include sulfonation, biotinylation, or the addition of other moieties, particularly those which have molecular shapes similar to phosphate groups.

Analogs of the mammalian galanin receptors can be prepared by chemical synthesis or by using site-directed mutagenesis [Gilman et al., *Gene* 8:81 (1979); Roberts et al., *Nature* 328:731 (1987) or his (Ed.), 1990, *PCR Protocols: A Guide to Methods and Applications*, Academic Press, New York, N.Y.] or the polymerase chain reaction method [PCR; Saiki et al., *Science* 239:487 (1988)], as exemplified by Daugherty et al. [*Nucleic Acids Res.* 19:2471 (1991)] to modify nucleic acids encoding the complete receptors. Adding epitope tags for purification or detection of recombinant products is envisioned.

General techniques for nucleic acid manipulation and expression that can be used to make the analogs are described generally, e.g., in Sambrook, et al., *Molecular Cloning: A Laboratory Manual* (2d ed.), 1989, Vols. 1-3, Cold Spring Harbor Laboratory. Techniques for the synthesis of polypeptides are described, for example, in Merrifield, *J. Amer. Chem. Soc.* 85:2149 (1963); Merrifield, *Science* 232:341 (1986); and Atherton et a., *Solid Phase Peptide Synthesis: A Practical Approach,* 1989, IRL Press, Oxford.

Still other analogs are prepared by the use of agents known in the art for their usefulness in cross-linking proteins through reactive side groups. Preferred derivatization sites with cross-linking agents are free amino groups, carbohydrate moieties and cysteine residues.

Substantial retention of ligand binding activity by the foregoing analogs of the mammalian galanin receptors typically entails retention of at least about 50%, preferably at least about 75%, more preferably at least about 80%, and most preferably at least about 90% of the galanin binding activity and/or specificity of the corresponding wild-type receptor.

Some of the physical variants have substantial amino acid sequence homology with the amino acid sequences of the mammalian galanin receptors or polypeptides. In this invention, amino acid sequence homology, or sequence identity, is determined by optimizing residue matches and, if necessary, by introducing gaps as required. Homologous amino acid sequences are typically intended to include natural allelic, polymorphic and interspecies variations in each respective sequence.

Typical homologous proteins or peptides will have from 25-100% homology (if gaps can he introduced) to 50-100% homology (if conservative substitutions are included), with he amino acid sequence of the galanin receptors. Primate species receptors are of particular interest.

Observed homologies will typically be at least about 35%, preferably at least about 50%, more preferably at least about 75%, and most preferably at least about 80% or more. See Needleham et al, *J. Mol. Biol.* 48:443-453 (1970); Sankoff et al. in *Time Warps, String Edits, and Macromolecules: The Theory and Practice of Sequence Comparison,* 1983, Addison-Wesley, Reading, Mass.; and software packages from IntelliGenetics, Mountain View, Calif., and the University of Wisconsin Genetics Computer Group, Madison, Wis.

Glycosylation variants include, e.g., analogs made by modifying glycosylation patterns during synthesis and processing in various alternative eukaryotic host expression systems, or during further processing steps. Particularly preferred methods for producing glycosylation modifications include exposing the mammalian galanin receptors to glycosylating enzymes derived from cells which normally carry out such processing, such as mammalian glycosylation enzymes. Alternatively, deglycosylation enzymes can be used to remove carbohydrates attached during production in eukaryotic expression systems.

Protein Purification

The proteins, polypeptides and antigenic fragments of this invention can be purified by standard methods, including but not limited to salt or alcohol precipitation, preparative disc-gel electrophoresis, isoelectric focusing, high pressure liquid chromatography (HPLC), reversed-phase HPLC, gel filtration, cation and anion exchange and partition chromatography, and countercurrent distribution. Such purification methods are well known in the art and are disclosed, e.g., in *Guide to Protein Purification, Methods in Enzymology*, Vol. 182, M. Deutscher, Ed., 1990, Academic Press, New York, N.Y. More specific methods applicable to purification of the galanin receptors are described below.

Purification steps can be followed by carrying out assays for ligand binding activity as described below. Particularly where a receptor is being isolated from a cellular or tissue source, it is preferable to include one or more inhibitors of proteolytic enzymes is the assay system, such as phenylmethanesulfonyl fluoride (PMSF).

Antibody Production

Antigenic (i.e., immunogenic) fragments of the mammalian galanin receptors of this invention, which may or may not have ligand binding activity, may similarly be produced. Regardless of whether they bind galanin, such fragments, like the complete receptors, are useful as antigens for preparing antibodies by standard methods that can bind to the complete receptors. Shorter fragments can be concatenated or attached to a carrier. Because it is well known in the art that epitopes generally contain at least about five, preferably at least about S, amino acid residues [Ohno et al., *Proc. Natl. Acad. Sci. USA* 82:2945 (1985)], fragments used for the production of antibodies will generally be at least that size. Preferably, they will contain even more residues, as described above. Whether a given fragment is immunogenic can readily be determined by routine experimentation.

Although it is generally not necessary when complete mammalian galanin receptors are used as antigens to elicit antibody production in an immunologically competent host, smaller antigenic fragments are preferably first rendered more immunogenic by cross-linking or concatenation, or by coupling to an immunogenic carrier molecule (i.e., a macromolecule having the property of independently eliciting an immunological response in a host animal). Cross-linking or conjugation to a carrier molecule may be required because small polypeptide fragments sometimes act as haptens (molecules which are capable of specifically binding to an antibody but incapable of eliciting antibody production, i.e., they are not immunogenic). Conjugation of such fragments to an immunogenic carrier molecule renders them more immunogenic through what is commonly known as the "carrier effect".

Suitable carrier molecules include, e.g., proteins and natural or synthetic polymeric compounds such as polypeptides, polysaccharides, lipopolysaccharides etc. Protein carrier molecules are especially preferred, including but not limited to keyhole limpet hemocyanin and mammalian serum proteins such as human or bovine gammaglobulin, human, bovine or rabbit serum albumin, or methylated or other derivatives of such proteins. Other protein carriers will be apparent to those skilled in the art. Preferably, but not necessarily, the protein carrier will be foreign to the host animal in which antibodies against the fragments are to be elicited.

Covalent coupling to the carrier molecule can be achieved using methods well known in the art, the exact choice of which will be dictated by the nature of the carrier molecule used. When the immunogenic carrier molecule is a protein, the fragments of the invention can be coupled, e.g., using water soluble carbodiimides such as dicyclohexylcarbodiimide or glutaraldehyde.

Coupling agents such as these can also be used to cross-link the fragments to themselves without the use of a separate carrier molecule. Such cross-linking into aggregates can also increase immunogenicity. Immunogenicity can also be increased by the use of known adjuvants, alone or in combination with coupling or aggregations.

Suitable adjuvants for the vaccination of animals include but are not limited to Adjuvant 65 (containing peanut oil, mannide monooleate and aluminum monostearate); Freund's complete or incomplete adjuvant; mineral gels such as aluminum hydroxide, aluminum phosphate and alum; surfactants such as hexadecylamine, octadecylamine, lysolecithin, dimethyldioctadecylammonium bromide, N,N-dicetadecyl-N',N'-bis(2-hydroxyethyl) propanediamine, methoxyhexadecylglycerol and pluronic polyols; polyanions such as pyran, dextran sulfate, poly IC, polyacrylic acid and carbopol; peptides such as muramyl dipeptide, dimethylolycine and tuftsin; and oil emulsions. The polypeptides could also be administered following incorporation into liposomes or other microcarriers.

Information concerning adjuvants and various aspects of immunoassays are disclosed, e.g., in the series by P. Tijssen, *Practice and Theory of Enzyme Immunoassays,* 3rd Edition, 1987, Elsevier, N.Y. Other useful references covering methods for preparing polyclonal antisera include *Microbiology,* 1969, Hoeber Medical Division, Harper and Row; Landsteiner, *Specificity of Serological Reactions,* 1962, Dover Publications, New York, and Williams, et al., *Methods in Immunology and Immunochemistry,* Vol. 1, 1967, Academic Press, New York.

Serum produced from animals immunized using standard methods can be used directly, or the IgC fraction can be separated from the serum using standard methods such as plasmaphoresis or adsorption chromatography with IgG-specific adsorbents such as immobilized Protein A. Alternatively, monoclonal antibodies can be prepared.

Hybridomas producing monoclonal antibodies against the galanin receptors of the invention or antigenic fragments thereof are produced by well-known techniques. Usually, the process involves the fusion of an immortalizing cell line with a B-lymphocyte that produces the desired antibody. Alternatively, non-fusion techniques for generating immortal antibody-producing cell lines can be used, e.g., virally-induced transformation [Casali et al., *Science* 234:476 (1986)]. Immortalizing cell lines are usually transformed mammalian cells, particularly myeloma cells of rodent, bovine, and human origin. Most frequently, rat or mouse myeloma cell lines are employed as a matter of convenience and availability.

Techniques for obtaining antibody-producing lymphocytes from mammals injected with antigens are well known. Generally, peripheral blood lymphocytes (PBLs) are used if cells of human origin are employed, or spleen or lymph node cells are used from non-human mammalian sources. A host animal is injected with repeated dosages of the purified antigen (human cells are sensitized in vitro), and the animal is permitted to generate the desired antibody-producing cells before they are harvested for fusion with the immortalizing cell line. Techniques for fusion are also well known in the art, and in general involve mixing the cells with a fusing agent, such as polyethylene glycol.

Hybridomas are selected by standard procedures, such as HAT (hypoxanthine-aminopterin-thymidine) selection. Those secreting the desired antibody are selected using standard immunoassays, such as Western blotting, ELISA (enzyme-linked immunosorbent assay), RIA (radioimmunoassay), or the like. Antibodies are recovered from the medium using standard protein purification techniques [Tijssen, *Practice and Theory of Enzyme Immunoassays* (Elsevier, Amsterdam, 1985)].

Many references are available to provide guidance in applying the above techniques [Kohler et al. Hybridoma Techniques (Cold Spring Harbor Laboratory, New York, 1980); Tijssen, *Practice and Theory of Enzyme Immunoassays* (Elsevier, Amsterdam, 1985); Campbell, *Monoclonal Antibody Technology* (Elsevier, Amsterdam, 1984); Hurrell, *Monoclonal Hybridoma Antibodies: Techniques and Applications* (CRC Press, Boca Raton, Fla., 1982)]. Monoclonal antibodies can also be produced using well known phage library systems. See, e.g., Huse, et al., *Science* 246:1275 (1989); Ward, et al., *Nature* 341:544 (1989).

Antibodies thus produced, whether polyclonal or monoclonal, can be used, e.g., in an immobilized form bound to a solid support by well known methods, to purify the receptors by immunoaffinity chromatography.

Antibodies against the antigenic fragments can also be used, unlabeled or labeled by standard methods, as the basis for immunoassays of the mammalian galanin receptors. The particular label used will depend upon the type of immunoassay. Examples of labels that can be used include but are not limited to radiolabels such as $^{32}P$, $^{125}I$, $^{3}H$ and $^{14}C$; fluorescent labels such as fluorescein and its derivatives, rhodamine and its derivatives, dansyl and umbelliferone; chemilluminescers such as luciferase and 2,3-dihydrophthalazinediones; and enzymes such as horseradish peroxidase, alkaline phosphatase, lysozyme and glucose-6-phosphate dehydrogenase.

The antibodies can be tagged with such labels by known methods. For example, coupling agents such as aldehydes, carbodiimides, dimaleimide, imidates, succinimides, bisdiazotized benzadine and the like may be used to tag the antibodies with fluorescent, chemilluminescent or enzyme labels. The general methods involved are well known in the art and are described, e.g., in *Immunoassay: A Practical Guide,* 1987, Chan (Ed.), Academic Press, Inc., Orlando, Fla. Such immunoassays could be carried out, for example, on fractions obtained during purification of the receptors.

The antibodies of the present invention can also be used to identify particular cDNA clones expressing the galanin receptors in expression cloning systems.

Neutralizing antibodies specific for the ligand binding site of a receptor can also be used as antagonists (inhibitors) to block galanin binding. Such neutralizing antibodies can readily be identified through routine experimentation, e.g., by using the radioligand binding assay described infra. Antagonism of galanin activity can be accomplished using complete antibody molecules, or well known antigen binding fragments such as Fab, Fc, F(ab)$_2$, and Fv fragments.

Definitions of such fragments can be found, e.g., in Klein, *Immunology* (John Wiley, New York, 1982); Parham. Chapter 14, in Weir, ed. *Immunochemistry* 4th Ed. (Blackwell Scientific Publishers, Oxford, 1986). The use and generation of antibody fragments has also been described, e.g.: Fab fragments [Tijssen, *Practice and Theory of Enzyme Immunoassays* (Elsevier, Amsterdam, 1985)], Fv fragments [Hochman et al., Biochemistry 12:1130 (1973); Sharon e al., Biochemistry 15:1591 (1976); Ehrlich et al., U.S. Pat. No. 4,355,023] and antibody half molecules (Auditore-Hargeaves, U.S. Pat. No. 4,470,925). Methods for making recombinant Fv fragments based on known antibody heavy and light chain variable region sequences have further been described, e.g., by Moore et al. (U.S. Pat. No. 4,642,334) and by Plückthun [*Bio/Technology* 9:545 (1991)]. Alternatively, they can be chemically synthesized by standard methods.

Anti-idiotypic antibodies, both polyclonal and monoclonal, can also be produced using the antibodies elicited against the receptors as antigens. Such antibodies can be useful as they may mimic the receptors.

Nucleic Acids and Expression Vectors

As used herein, the term "isolated nucleic acid" means a nucleic acid such as an RNA or DNA molecule, or a mixed polymer, which is substantially separated from other components that are normally found in cells or in recombinant DNA expression systems. These components include but are not limited to ribosomes, polymerases, serum components, and flanking genomic sequences. The term thus embraces a nucleic acid which has been removed from its naturally occurring environment, and includes recombinant or cloned DNA isolates and chemically synthesized analogs or analogs biologically synthesized by heterologous systems. A substantially pure molecule includes isolated forms of the molecule.

An isolated nucleic acid will generally be a homogeneous composition of molecules but may, in some embodiments, contain minor heterogeneity. Such heterogeneity is typically found at the ends of nucleic acid coding sequences or in regions not critical to a desired biological function or activity.

A "recombinant nucleic acid" is defined either by its method of production or structure. Some recombinant nucleic acids are thus made by the use of recombinant DNA techniques which involve human intervention, either in manipulation or selection. Others are made by fusing two fragments not naturally contiguous to each other. Engineered vectors are encompassed, as well as nucleic acids comprising sequences derived using any synthetic oligonucleotide process.

For example, a wild-type codon may be replaced with a redundant codon encoding the same amino acid residue or a conservative substitution, while at the same time introducing or removing a nucleic acid sequence recognition site. Similarly, nucleic acid segments encoding desired functions may be fused to generate a single genetic entity encoding a desired combination of functions not found together in nature. Although restriction enzyme recognition sites are often the target of such artificial manipulations, other site-specific targets, e.g., promoters, DNA replication sites, regulation sequences, control sequences, or other useful features may be incorporated by design. Sequences encoding epitope tags for detection or purification as described above may also be incorporated.

A nucleic acid "fragment" is defined herein as a nucleotide sequence comprising at least about 17, generally at least about 25, preferably at least about 35, more preferably at least about 45, and most preferably at least about 55 or more contiguous nucleotides.

This invention further encompasses recombinant DNA molecules and fragments having sequences that are identical or highly homologous to those described herein. The nucleic acids of the invention may be operably linked to DNA segments which control transcription, translation, and DNA replication, "Homologous nucleic acid sequences" are those which when aligned and compared exhibit significant similarities. Standards for homology in nucleic acids are either measures for homology generally used in the art by sequence comparison or based upon hybridization conditions, which are described in greater detail below.

Substantial nucleotide sequence homology is observed when there is identity in nucleotide residues in two sequences (or in their complementary strands) when optimally aligned to account for nucleotide insertions or deletions, in at least about 50%, preferably in at least about 75%, more preferably in at least about 90%, and most preferably in at least about 95% of the aligned nucleotides.

Substantial homology also exists when one sequence will hybridize under selective hybridization conditions to another. Typically, selective hybridization will occur when there is at least about 55% homology over a stretch of at least about 30 nucleotides, preferably at least about 65% over a stretch of at least about 25 nucleotides, more preferably at least about 75%, and most preferably at least about 90% over about 20 nucleotides. See, e.g., Kanehisa, *Nucleic Acids Res.* 12:203 (1984).

The lengths of such homology comparisons may encompass longer stretches and in certain embodiments may cover a sequence of at least about 17, preferably at least about 25, more preferably at least about 50, and most preferably at least about 75 nucleotide residues.

Stringency of conditions employed in hybridizations to establish homology are dependent upon factors such as salt concentration, temperature, the presence of organic solvents, and other parameters. Stringent ten premature conditions usually include temperatures in excess of about 30° C., often in excess of about 37° C., typically in excess of about 45° C., preferably in excess of about 55° C., more preferably in excess of about 65° C., and most preferably in excess of about 70° C. Stringent salt conditions will ordinarily be less than about 1000 mM, usually less than about 500 mM, more usually less than about 400 mM, preferably less than about 300 mM, more preferably less than about 200 mM, and most preferably less than about 150 mM. For example, salt concentrations of 100, 50 and 20 mM are used. The combination of the foregoing parameters, however, is more important that the measure of any single parameter. See, e.g., Wetmur et al, *J. Mol. Biol.* 31:349 (1968).

The term "substantially pure" is defined herein to mean a mammalian galanin receptor, nucleic acid or other material that is free from other contaminating proteins, nucleic acids, and other biologicals derived from an original source organism or recombinant DNA expression system. Purity may be assayed by standard methods and will typically exceed at least about 50%, preferably at least about 75%, more preferably at least about 90%, and most preferably at least about 95% purity. Purity evaluation may be made on a mass or molar basis.

Nucleic acids encoding the galanin receptors or fragments thereof can be prepared by standard methods. For example, DNA can be chemically synthesized using, e.g., the phosphoramidite solid support method of Matteucci et al. [*J. Am. Chem. Soc.* 103:3185 (1981)], the method of Yoo et at. [*J. Biol. Chem.* 764:17078 (1989)], or other well known methods. This can be done by sequentially linking a series of oligonucleotide cassettes comprising pairs of synthetic oligonucleotides, as described below.

Of course, due to the degeneracy of the genetic code, many different nucleotide sequences can encode the galanin receptors. The codons can be selected for optimal expression in prokaryotic or eukaryotic systems. Such degenerate variants are of course also encompassed by this invention.

Moreover, nucleic acids encoding the galanin receptors can readily be modified by nucleotide substitutions, nucleotide deletions, nucleotide insertions, and inversions of nucleotide stretches. Such modifications result in novel DNA sequences which encode antigens having immunogenic or antigenic activity in common with the wild-type receptors. These modified sequences can be used to produce wild-type or mutant receptors, or to enhance expression in a recombinant DNA system.

Insertion of the DNAs encoding the galanin receptors into a vector is easily accomplished when the termini of both the DNAs and the vector comprise compatible restriction sites. If this cannot be done, it may be necessary to modify the termini of the DNAs and/or vector by digesting back single-stranded DNA overhangs generated by restriction endonuclease cleavage to produce blunt ends, or to achieve the same result by filling in the single-stranded termini with an appropriate DNA polymerase.

Alternatively, desired sites may be produced, e.g., by ligating nucleotide sequences (linkers) onto the termini. Such linkers may comprise specific oligonucleotide sequences that define desired restriction sites. Restriction sites can also be generated by the use of the polymerase chain reaction (PCR). See, e.g., Saiki et al., *Science* 239:487 (1988). The cleaved vector and the DNA fragments may also be modified if required by homopolymeric tailing.

Recombinant expression vectors used in this invention are typically self-replicating DNA or RNA constructs comprising nucleic acids encoding one of the mammalian GalR3 receptors, usually operably linked to suitable genetic control elements that are capable of regulating expression of the nucleic acids in compatible host cells. Genetic control elements may include a prokaryotic promoter system or a eukaryotic promoter expression control system, and typically include a transcriptional promoter, an optional operator to control the onset of transcription, transcription enhancers to elevate the level of mRNA expression, a sequence that encodes a suitable ribosome binding site, and sequences that terminate transcription and translation. Expression vectors also may contain an origin of replication that allows the vector to replicate independently of the host cell.

Vectors that could be used in this invention include microbial plasmids, viruses, bacteriophage, integratable DNA fragments, and other vehicles which may facilitate integration of the nucleic acids into the genome of the host. Plasmids are the most commonly used form of vector but all other forms of vectors which serve an equivalent function and which are, or become, known in the art are suitable for use herein. See, e.g., Pouwels et al., *Cloning Vectors: A Laboratory Manual*, 1985 and Supplements, Elsevier, N.Y., and Rodriguez et al. (eds.), *Vectors: A Survey of Molecular Cloning Vectors and Their Uses*, 1988, Buttersworth, Boston, Mass.

Expression of nucleic acids encoding the galanin receptors of this invention can be carried out by conventional methods in either prokaryotic or eukaryotic cells. Although strains of *E. coli* are employed most frequently in prokaryotic systems, many other bacteria such as various strains of *Pseudomonas* and *Bacillus* are know in the art and can be used as well.

Prokaryotic expression control sequences typically used include promoters, including those derived from the β-lactamase and lactose promoter systems [Chang et at, *Nature* 198:1056 (1977)], the tryptophan (trp) promoter system [Goeddel et al., *Nucleic Acids Res.* 8:4057 (1980)], the lambda $P_L$ promoter system [Shimatake et. al., *Nature* 292:128 (1981)] and the tac promoter [De Boer et al., *Proc. Natl. Acad. Sci. USA* 292:128 (1983)]. Numerous expression vectors containing such control sequences are known in the art and and available commercially.

Suitable host cells for expressing nucleic acids encoding the mammalian GalR3 receptors include prokaryotes and higher eukaryotes. Prokaryotes include both gram negative and positive organisms, e.g., *E. coli* and *B. stubtilis*. Higher eukaryotes include established tissue culture cell lines from animal cells, both of non-mammalian origin, e.g., insect cells, and birds, and of mammalian origin, e.g., human, primates and rodents.

Prokaryotic host-vector systems include a wide variety of vectors for many different species. As used herein, *E. coli* and its vectors will be used generically to include equivalent vectors used in other prokaryotes. A representative vector for amplifying DNA is pBR322 or many of its derivatives. Vectors that can be used to express the mammalian GalR3 receptors include but are not limited to those containing the lac promoter (pUC-series); tp promoter (pBR322-trp); Ipp promoter (the pIN-series); lambda-pP or pR promoters (pOTS); or hybrid promoters such as ptac (pDR540). See Brosius et al., "Expression Vectors Employing Lambda-, trp-, lac-, and Ipp-derived Promoters", in Rodriguez and Denhardt (eds.) *Vectors: A Survey of Molecular Cloning Vectors and Their Uses*, 1988, Buttersworth, Boston, pp. 205-236.

Higher eukaryotic tissue culture cells are preferred hosts for the recombinant production of the mammalian GalR3 receptors. Although any higher eukaryotic tissue culture cell line might be used, including insect baculovirus expression systems, mammalian cells are preferred. Transformation or transfection and propagation of such cells has become a routine procedure. Examples of useful cell lines include HeLa cells, Chinese hamster ovary (CHO) cell lines, baby rat kidney (BRK) cell lines, insect cell lines, bird cell lines, and monkey (COS) cell lines.

Expression vectors for such cell lines usually include an origin of replication, a promoter, a translation initiation site, RNA splice sites (if genomic DNA is used), a polyadenylation site, and a transcription termination site. These vectors also usually contain a selection gene or amplification gene. Suitable expression vectors may be plasmids, viruses, or retroviruses carrying promoters derived, e.g., from such sources as adenovirus, SV40, parvoviruses, vaccinia virus, or cytomegalovirus. Representative examples of suitable expression vectors include pCR® 3.1, pCDNA1, pCD [Okayama et al., *Mol. Cell Biol.* 5:1136 (1985)], pMC1neo Poly-A [Thomas et a., *Cell* 51:503 (1987)], pUC19, pREP8, pSVSPORT and derivatives thereof, and baculovirus vectors such as pAC 373 or pAC 610.

Pharmaceutical Compositions

The antibodies and antigen-binding fragments thereof can be used therapeutically to block the activity of galanin, and thereby to treat any medical condition caused or mediated by galanin. Such antibodies and fragments are preferably chimeric or humanized, to reduce antigenicity and human anti-mouse antibody (HAMA) reactions. The methodology involved is disclosed, e.g., in U.S. Pat. No. 4,816,397 to Boss et al. and in U.S. Pat. No. 4,816,567 to Cabilly et at. Further refinements on antibody humanization are described in European Patent 451 216 B1.

The dosage regimen involved in a therapeutic application will be determined by the attending physician, considering various factors which may modify the action of the antibodies or binding fragments, e.g., the condition, body weight, sex and diet of the patient, the severity of any infection, time of administration, and other clinical factors.

Typical protocols for the therapeutic administration of antibodies are well known in the an and have been disclosed, e.g., by Elliott et al [*The Lancet* 344:1125 (1994)], Isaacs et al. [*The Lancet* 340:748 (1992)], Ansetti et al. [*Transplantation* 54:844 (1992)], Anasetti et al. [*Blood* 84:1320 (1994)], Hale et. al. [*The Lancet* 2:1394 (Dec. 17, 1988)], Queen [*Scrip* 1881:18 (1993)] and Mathieson et al. [*N. Eng. J. Med.* 323:250 (1990)].

Administration of the compositions of this invention is typically parenteral, by intraperitoneal, intravenous, subcutaneous, or intramuscular injection, or by infusion or by any other acceptable systemic method. Administration by intravenous infusion, typically over a time course of about 1 to 5 hours, is preferred.

Often, treatment dosages are titrated upward from a low level to optimize safety and efficacy. Generally, daily antibody dosages will fall within a range of about 0.01 to 20 mg protein per kilogram of body weight. Typically, the dosage range will be from about 0.1 to 5 mg protein per kilogram of body weight.

Dosages of antigen binding fragments from the antibodies will be adjusted to account for the smaller molecular sizes and possibly decreased half-lives (clearance times) following administration. Various modifications or derivatives of the antibodies or fragments, such as addition of polyethylene glycol chains (PEGylation), may be made to influence their pharmacokinetic and/or pharmacodytinic properties.

It will be appreciated by those skilled in the art, however, that the galanin antagonists of the invention are not limited to neutralizing antibodies or binding fragments thereof This invention also encompasses other types of inhibitors, including small organic molecules and inhibitory ligand analogs, which can be identified using the methods of the invention.

An "effective amount" of a composition of the invention is an amount that will ameliorate one or more of the well known parameters that characterize medical conditions caused or mediated by galanin. Many such parameters and conditions have been described, e.g., as in reviews by Bantfa (*Psychopharmacology: The Fourth Generation of Progress*, 1995, F. E. Bloom and D. J. Kupfer, Eds., Ravin Press, Ltd., New York, N.Y., pp. 563-571) and Crawley [*Life Science* 58:2185-2199 (1996)].

Although the compositions of this invention could be administered in simple solution, they are more typically used in combination with other materials such as carriers, preferably pharmaceutical carriers. Useful pharmaceutical carriers can be any compatible, non-toxic substance suitable for delivering the compositions of the invention to a patient. Sterile water, alcohol, fats, waxes, and inert solids may be included in a carrier. Pharmaceutically acceptable adjuvants (buffering agents, dispersing agents) may also be incorporated into the pharmaceutical composition. Generally, compositions useful for parenteral administration of such drugs are well known; e.g. *Remington's Pharmaceutical Science*, 17th Ed. (Mack Publishing Company, Easton, Pa., 1990). Alternatively, compositions of the invention may be introduced into a patient's body by implantable drug delivery systems [Urquhart et al., *Ann. Rev. Pharmacol. Toxicol.* 24:199 (1984)].

Therapeutic formulations may be administered in many conventional dosage formulation. Formulations typically comprise at least one active ingredient, together with one or more pharmaceutically acceptable carriers. Formulations may include those suitable for oral, rectal, nasal, or parenteral (including subcutaneous, intramuscular, intravenous and intradermal) administration.

The formulations may conveniently be presented in unit dosage form and may be prepared by any methods well known in the art of pharmacy. See, e.g., Gilman et al. (eds.) (1990), *The Pharmacological Bases of Therapeutics*, 8th Ed., Pergamon Press; and *Remington's Pharmaceutical Sciences*, supra, Easton, Pa.; Avis et al. (eds.) (1993) *Pharmaceutical Dosage Forms: Parenteral Medications* Dekker, N.Y.; Lieberman et al. (eds.) (1990) *Pharmaceutical Dosage Forms: Tablets* Dekker, N.Y.; and Liebe et al. (eds.) (1990), *Pharmaceutical Dosage Forms: Disperse Systems* Dekker, N.Y.

The present invention also encompasses anti-idiotypic antibodies, both polyclonal and monoclonal, which are produced using the above-described antibodies as antigens. These antibodies are useful because they may mimic the structures of the receptors.

Screening Systems and Method

The galanin receptors of this invention can be employed in screening systems to identify agonists or antagonists of the receptors. Essentially, these systems provide methods for bringing together a mammalian galanin receptor, an appropriate known ligand, including galanin itself, and a sample to be tested for the presence of a galanin agonist or antagonist.

Two basic types of screening systems can be used, a labeled-ligand binding assay and a "functional" assay. A labeled ligand for use in the binding assay can be obtained by labeling galanin or a known galanin agonist with a measurable group as described above in connection with the labeling of antibodies. Various labeled forms of galanin are available commercially. In an example below, $^{125}$I-galanin is used as the ligand.

Typically, a given amount of one of the galanin receptors of the invention is contacted with increasing amounts of a labeled ligand, such as labeled galanin itself, and the amount of the bound labeled ligand is measured after removing unbound labeled ligand by washing. As the amount of the labeled ligand is increased, a point is eventually reached at which all receptor binding sites are occupied or saturated. A plot of such binding is shown in FIG. 1. Specific receptor binding of the labeled ligand is abolished by a large excess of unlabeled ligand.

Preferably an assay system is used in which non-specific binding of the labeled ligand to the receptor is minimal. Nonspecific binding is typically less than 50%, preferably less than 15%, and more preferably less than 10% of the total binding of the labeled ligand.

As used herein, the term "gal in ligand" is defined to mean galanin itself or a fragment thereof comprising at least about the fifteen amino-terminal residues of galanin, and extending up to the complete galanin molecule. The amino acid sequence of the amino-terminal residues is conserved in the galanins of various species, including humans. Therefore, galanin from one species may bind to galanin receptors from another species; e.g., porcine galanin binds to the rat receptor, as is illustrated in an Example below. For regulatory purposes, however, it may be desirable to use human galanin or an active fragment thereof as the galanin ligand in conjunction with the human receptor when screening for galanin agonists or antagonists for human therapeutic purposes.

In principle, a binding assay of the invention could be carried out using a soluble receptor of the invention, e.g., following production and refolding by standard methods from an *E. coli* expression system, and the resulting receptor-labeled ligand complex could be precipitated, e.g., using an antibody against the receptor. The precipitate could then be washed and the amount of the bound labeled ligand could be measured.

Preferably, however, a nucleic acid encoding one of the galanin receptors of the invention is transfected into an appropriate host cell, whereby the receptor will become incorporated into the membrane of the cell. A membrane fraction can then be isolated from the cell and used as a source of the receptor for assay. Preferably, specific binding of the labeled ligand to a membrane fraction from the untransfected host cell will be negligible, as is the case with COS-7 cells used in an Example below.

The binding assays of this invention can be used to identify both galanin agonists and antagonists, because both will compete for binding to the receptor with the labeled ligand.

In the basic binding assay, the method for identifying a galanin agonist or antagonist comprises:
(a) contacting a mammalian GalR3 receptor having an amino acid sequence defined by SEQ ID NO: 2 or SEQ ID NO. 4, or a subsequence thereof, in the presence of a known amount of labeled galanin with a sample to be tested for the presence of a galanin agonist or antagonist; and
(b) measuring the amount of labeled galanin bound to the receptor;

whereby a galanin agonist or antagonist in the sample is identified by measuring substantially reduced binding of the labeled galanin to the GalR3 receptor, compared to what would be measured in the absence of such agonist or antagonist.

Preferably, the GalR3 receptor used to identify a galanin agonist or antagonist for human therapeutic purposes has an amino acid sequence defined by SEQ ID NO: 4, or a subsequence thereof.

In one embodiment of the invention, the foregoing method further comprises:
(c) contacting a mammalian GalR1 or GalR2 receptor in the presence of a known amount of labeled galanin with a compound identified as a galanin agonist or antagonist in steps (a) and (b); and
(d) measuring the amount of labeled galanin bound to the receptor;

whereby a galanin agonist or antagonist specific for the GalR3 receptor is identified by measuring substantially undiminished binding of the labeled galanin to the receptor, compared to what would be measured in the absence of such agonist or antagonist.

Determination of whether a particular molecule inhibiting binding of the labeled ligand to the receptor is an antagonist or an agonist is then determined in a second, functional assay. The functionality of GalR3 agonists and antagonists identified in the binding assay can be determined in cellular and animal models.

In cellular models, parameters for intracellular activities mediated by galanin receptors can be monitored for antagonistic and/or agonistic activities. Such parameters include but are not limited to intracellular second messenger pathways activated via the GdaR3 receptors, changes in cell growth rate, secretion of hormones, etc., using published methods. Examples of the methods are measurement of the effects of the ligands on receptor-mediated inhibition of forskolin-stimulated intracellular cAMP production [Parker et al, *Mol. Brain Res.* 34:179-189 (1995)], receptor-stimulated $Ca^{++}$ mobilization and mitogenic effects [Sethi et al. *Cancer Res.* 51:1674-1679 (1991)], and receptor-mediated glucose-stimulated insulin release [Yanaihara et al., *Regulatory Peptides* 46:93-101 (1993)].

In animal models, physiological effects of the agonists and antagonists can be evaluated by feeding the compounds and observing changes in feeding behavior and body weight [Crawley et al, *Brain Res.* 600:268-272 (1993)], acetylcholine release [Ogren et al., *Eur. J. Pharmacology* 242:59-64 (1993)], learning [Ogren et at, *Neuroscience* 51:1-5 (1992)], memory [Robinsin et a., *Behav. Neurosci.* 107:458-467 (1993)], and pain modulation [Verge et al., *Neuroscience Letters* 149:193-197 (1993)].

Other Mammalian GalR3 Receptors

The present invention provides methods for cloning mammalian GalR3 receptors from other mammalian species. Briefly, Southern and Northern blot analysis can be carried out to identify cells from other species expressing genes encoding the GalR3 receptors, Complementary DNA (cDNA) libraries can be prepared by standard methods from mRNA isolated from such cells, and degenerate probes or PCR primers based on the nucleic acid and amino acid sequences provided herein can be used to identify clones encoding a GalR3 receptor.

Alternatively, expression cloning methodology can be used to identify particular clones encoding a GalR3 receptor. An antibody preparation which exhibits cross-reactivity with GalR3 receptors from a number of mammalian species may be useful in monitoring expression cloning.

However identified, clones encoding GalR3 receptors from various mammalian species can be isolated and sequenced, and the coding regions can be excised and inserted into an appropriate vector.

EXAMPLES

The present invention can be illustrated by the following examples. Unless otherwise indicated, percentages given below for solids in solid mixtures, liquids in liquids, and solids in liquids are on a wt/wt, vol/vol and wt/vol basis, respectively. Sterile conditions were generally maintained during cell culture.

Materials and General Methods $^{125}$I-porcine galanin (2200 Ci/mmol) was purchased from DuPont-NEN (Boston, Mass.). Various PCR/RACE oligonucleotide primers were custom synthesized by BRL Life Technologies (Grand Island, N.Y.). MARATHON RACE cDNA was obtained from Clontech, Palo Alto, Calif. Rat galanin and C7 [*Brain Research* 600:268-272 (1993)] were purchased from Peninsula Laboratories (Belmont, Calif.). Rat galanin 92-29) and rat galanin(3-29) were custom synthesized by Bio-synthesis, Inc.

Cloning vector pCR® 2.1 and expression vector pCR® 3.1 were obtained from Invitrogen, San Diego, Calif. and used according to the manufacturer's instructions. TA cloning was carried out using pCR® 2.1, whereby PCR products were ligated into the prepared vector without prior restriction cleavage. Expression vector pCR® 3.1 containing cDNA encoding the mammalian GalR3 receptors was used to transfect COS cells. Human brain cDNA and human genomic DNA were from Clontech and Premega, respectively.

Standard methods were used, as described, e.g., in Maniatis et al., *Molecular Cloning: A Laboratory Manual,* 1982, Cold Spring Harbor Laboratory, Cold Spring Harbor Press; Sambrook et al., *Molecular Cloning: A Laboratory Manual,* (2d ed.), Vols 1-3, 1989, Cold Spring Harbor Press, NY; Ausubel et al., *Biology,* Greene Publishing Associates, Brooklyn, N.Y.; or Ausubel, et a. (1987 and Supplements), *Current Protocols in Molecular Biology,* Greene/Wiley, New York; Innis et al. (eds.) *PCR Protocols. A Guide to Methods and Applications,* 1990, Academic Press, N.Y.

The polymerase chain reaction (PCR) and rapid amplification of cDNA ends (RACE) were carried out using the Clontech protocols. Briefly, PCR was always run with KLENTAQ polymerase, which possesses proof reading activity (Clontech), and a cycling profile of 94° C. for 1 minute, 65° C. for 1 minute and 72° C. for 2 minutes (40 cycles). Approximately 1 µl of overnight *E. coli* cell culture was used in the PCR for sib selection.

For RACE, nested primers specific to the rat or human GalR3 cDNA and nested adaptor primers were used in the primary and secondary PCRs with about 0.1 µg of genomic or cDNA as a template. Thermal cycling at 94° C. for 30 seconds, 65° C. for 30 seconds and 72° C. for 90 seconds (25 cycles) was used in primary PCR. Cycling at 94° C. for 1 minute and 70° C. for 4 minutes (30 cycles) using 5 µl of the primary PCR product (diluted 1:50) as a template was used in the secondary PCR. A GC melt reagent (Clontech) at recommended dilution was always used in both PCR and RACE reactions.

DNA sequencing was performed with ABI Prism dye termination DNA sequencing reagents and an ABI automated sequencing apparatus (Perkin Elmer, Branchburg, N.J.) or manually with a SEQUITHERM ECCEL sequencing kit (Epicentre Technologies, Madison, Wis.). DNA and protein sequence comparisons were performed with DNA* software from DNAstar Inc., Madison, Wis.

A rat hypothalamous cDNA library was constructed by standard methods. Briefly, total RNA from rat hypothalamous was extracted with Tri-reagent-RNA/DNA/protein Isolation Reagent (Molecular Research Center, Cincinnati, Ohio. Poly $(A)^+$ RNA from the total RNA was purified with an mRNA purification kit employing oligo(dT)-cellulose chromatography (Pharmacia, Piscataway, N.J.). Double-stranded cDNA was synthesized from the poly$(A)^+$ RNA with a Marathon cDNA amplification kit (Clontech). A portion of the cDNA was blunt-end ligated with an adaptor containing a BstXI restriction site. The BstXI adaptor-linked cDNA was then ligated into a pCDNA3 vector predigested with BstXI.

Transfection was carried out as follows. Confluent COS-7 cells (ATCC CRL 1651) grown in DMEVI supplemented with 10% fetal calfserum (FCS) with 100 units/ml penicillin and 100 µg/ml streptomycin were split 1:6 into 150 mm dishes (Nunc) three days prior to transfection. On the day of transfection, the cells were approximately 90% confluent and trypsinized off plates and washed two times with PBS without $Mg^{++}$ and $Ca^{++}$. The cells were resuspended in Krebs Ringer's buffer at a density of approximately $1.2 \times 10^7$ cells/ml. Twenty µg of vector pCR® 3.1 containing rat GalR3 cDNA was diluted in Krebs Ringer's buffer (100 µl final volume), mixed with 0.7 ml of the COS-7 cells in a 0.4 cm electroporation cuvettes (Bio-rad, Hercules, Calif.) then chilled on ice for 5 min. The cells were electroporated at 960 µF×260 volts (time constant approximately 18) followed by incubation on ice for 10 min. The cells were incubated in DMEM with 10% FCS in a 150-mm plate.

Methods utilizing the Lipofectamine reagents (BRL Life Technologies) and the SuperFect reagents (Qiagene Inc., Chatsworth, Calif.) to transfect COS-7 cells worked equally well.

Example 1

Cloning and Characterization of the GalR3 Receptor

In a BLAST [Altschul et at, *J. Mol. Biol.* 215:403-410 (1990)] search of the GenBank data base with the human GalR1 receptor amino acid sequence (Habert-Ortoli et al., supra) as a query sequence, a portion of a clone having Accession No. Z82241 was found to possess high homology with the human GalR1 sequence. The clone, identified as J81I2, is a human genomic sequence partially sequenced and arranged in the database as 31 segments separated by thirty 800-n sequences in random order. Amino acid residues 64-132 of the human GalR1 receptor aligned with an amino acid sequence translated at the third reading frame on the positive strand of clone J81I2 with 55% identity. A smaller homologous match between amino acid residues 37-62 of the human GalR1 sequence and part of the translated nucleotide sequence of clone J81I2 (third reading frame on the positive strand) was also found to be 57% identical in the same analysis.

The homology level (55-57%) found with this clone is significantly higher than a 40% homology found between the GalR1 and GalR2 receptors, and markedly lower than those between the species homologues of GalR1 receptors among human, rat and mouse (>90%). Thus, part of the nucleotide sequence of clone J81I2 appeared to encode an amino acid sequence, corresponding to amino acid residues 37-132 of human GalR1, of a new human galanin receptor designated the human GalR3 receptor.

In brief, the strategy used to obtain cDNA encoding the rat GalR3 receptor was to generate several pairs of PCR primers, based on the human genomic clone, and to use them in RT-PCR with rat hypothalamus RNA as template to obtain a cDNA sequence of the GalR3 cDNA.

Two PCR primers, designated oligo93C (SEQ ID NO: 5) and oligo 120B (SEQ ID NO: 6), produced a PCR product of approximately 700 bp which was cloned into vector pCR® 3.1. The DNA sequence of the clone was compared with the nucleotide sequences in GenBank and the search results revealed, in rank order, the human genomic clone (Z82241), rGalR2, and hGalR1 as the most homologous sequences, with identities of 86%, 65% ad 63%, respectively. The rat clone thus appeared to be the species homolog of the putative human GalR3 cDNA.

To extend the cDN-A sequence toward the 5' and 3' directions, RACE and PCR sib selection were used. In RACE amplification, primers designated oligo172 (SEQ ID NO: 7) and AP1 (SEQ ID NO: 8; outer adaptor primer) were used in the primary PCR and others designated oligo177 (SEQ ID NO: 9) and AP2 (SEQ ID NO: 10; inner adaptor primer) were used in the secondary PCR. The final RACE product, ≈1.8 kb, contained part of the 5' end of rat GalR3 cDNA and the upstream 5' untranslated region.

In PCR sib selection, two primers designated oligo164 (SEQ ID NO: 11) and oligo167 (SEQ ID NO: 12) were used to screen a cDNA library constructed from rat hypothalamus. The library was pooled at a size of ≈5000 clones/pool, and DNA was prepared for each of the individual pools. A pool designated A28 gave a positive band amplified with the two primers and was sub-divided and screened until a single clone was obtained. That clone, designated A28-1, was 1.3 kb long and possessed most of the putative rat GalR3 cDNA.

A full-length rat GAlR3 cDNA clone was obtained by performing further sib selection on the rat hypothalamus cDNA library using primer oligo185 (SEQ ID NO: 13), based on the sequence of the 5' RACE product, and primer oligo184 (SEQ ID NO: 14), based on the sequence of clone A28-1. A single clone A5-3 selected from library pool A5 was obtained and sequenced. That clone was 2.2 kb long and contained all of the sequence of clone A28-1 and part of the 5' RACE product. A complete open reading frame (ORF) was identified in the clone, and the deduced amino acid sequence of the ORE consisted of 370 amino acids with a calculated molecular mass of 40.3 kDa.

Hydropathy analysis and comparison with other GalR receptors revealed seven putative transmembrane spanning domains (TMs) typical of C-protein coupled receptors. The GalR3 receptor also contains a single potential N-linked glycosylation site in the N-terminal region, two Cys residues in the first and second extracellular loops that form a putative disulfide bond in these receptors, and two Cys residues in the C-terminal region that may be involved in palmitoylation.

Example 2

Cloning and Characterization of the Human GalR3 Receptor

To obtain the cDNA of the human GalR3 receptor, primers designated oligo 93 (SEQ ID NO: 15) and oligo 94 (SEQ ID NO: 16) based on the human GalR3 nucleotide sequence (Z82241) were used in PCR to generate the fragment with cDNA prepared by reverse-transcrption of human brain cDNA (Clontech; 0.1 µg) and human placenta genomic DNA (Premega; 0.1 µg) as template. A single band PCR product of ≈300 bp in length, as analyzed with agarose gel electrophoresis, was generated in both PCR reactions. The PCR product obtained with genomic DNA as template was cloned into the pCR® 2.1 vector to produce a clone designated pCR2.1-f93/94, and sequencing analysis showed that the cloned fragment was identical to part of the putative GalR3 sequence in genomic clone J81I2.

A series of nested forward and reverse primers within this sequence and human brain cDNA linked with adapters at the to ends was then used in RACE PCR to obtain the upstream and downstream cDNA sequences covering the start and stop codons. A 5'-RACE product, 0.5 kb long, was obtained with oligo 134 (SEQ ID NO: 17) and oligo 135 (SEQ ID NO: 18) as the nested GalR3-specific primers and the two adaptor-specific primers AP1 (SEQ ID NO: 8) and AP2 (SEQ ID NO: 10). Similarly, an 1-kb 3'-RACE product was obtained with oligo 93B (SEQ ID NO: 19) and oligo 93C (SEQ ID NO: 5) as the nested GalR3-specific primers. Sequencing of these two fragments revealed an in-frame start codon in the 5'-RACE product and an in-frame stop codon in the 3'-RACE product.

The full length cDNA of the GalR3 receptor was obtained by PCR using human brain cDNA as template and primers designated oligo 154 (SEQ ID NO: 20) and oligo 159A (SEQ ID NO: 21) to produce the long form, and primers designated oligo 156 (SEQ ID NO: 22) and oligo 159A (SEQ ID NO: 21) to produce the short form of the human GalR3 receptor.

Example 3

Agonist/Antagonist Screening Assay

Receptor membranes were prepared as follows. COS-7 cells transfected as described above with vector pCR® 3.1 containing cDNA encoding the rat GalR3 receptor were incubated in DMEM with 10% FCS in 150 mm plates for 3 days in a humidified 5% $CO_2$ incubator, after which the medium was removed and the cells were washed three times with phosphate buffered saline (PBS).

To each plate, 5 ml of 5 mM Hepes buffer (pH 7.4), 0.1 mM PMSF, and 0.1 mg/ml bacitracin were added and incubated at room temperature for 15 minutes. The cells were scraped from the plates and centrifuged at 13,000×g for 15 minutes at 4° C. The resulting cell pellet was resuspended in 2 ml of 25 mM Tris-Cl (pH7.4) containing 0.2 mM PMSF by vortexing, and dispersed with a syringe attached with a #23 gauge needle. Protein concentrations were determined using a RCA (bicinchoninic acid) method (Pierce, Rockford, Ill.).

Binding of $^{125}$I-porcine-galanin to the membrane preparations was performed in a buffer containing 25 mM Tris-Cl (pH7.4), 1% bovine serim albumin (w/v), 0.1% bacitracin, 2 µg/ml leupeptin and 10 mM $MgCl_2$. Ligand saturation plots were perfored using 20 µg amounts of the membrane protein in a total volume of 200 µl using 3 µM cold galanin to determine nonspecific binding. Peptide competition studies were performed in a total volume of 200 µl, containing 20 µg of membrane protein and 0.3 nM $^{125}$I-porcine galanin. Incubations were carried out at room temperature for 1 hour and were terminated by rapid vacuum filtration through MULTI-SCREEN FB (glass fiber B) Filter Plates (Millipore, Bedford, Mass.) which had been pre-treated with 0.3% polyethylenimine to prevent non-specific binding of the radioligand to the filter. The filters were then washed three times with 100 µl of PBS (pH7.4). All data were analyzed using non-linear regression software (Prism, GraphPad, San Diego, Calif.), and the Ki was calculated using the method of Cheng and Prusoff [*Biochem. Pharmacol.* 22:3099-3108 (1973)].

Figure 2:
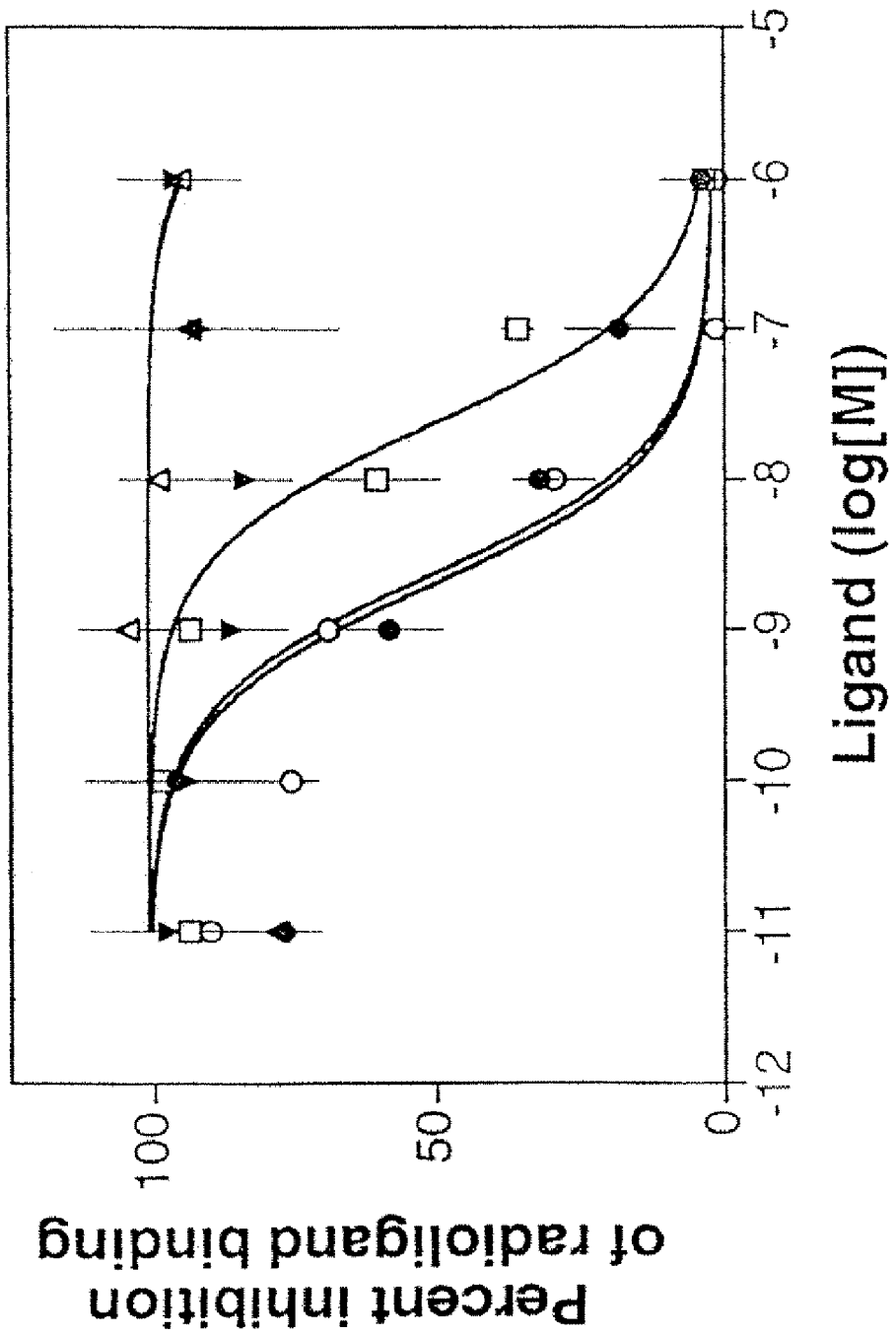
FIG. 2 is a graphical representation of the inhibition of the binding of $^{125}$I-porcine galanin to cellular receptors by various known galanin agonists and antagonists, showing percent inhibition of radioligand binding as a function of ligand concentration. The competing ligands were rat galanin (l), chimeric galanin peptide C7 (m), galanin(2-29) (o), galanin(3-29) (Δ) and galanin(10-20) (s).

In a typical assay, the results of which are shown in FIG. 2, the competing ligands rat galanin (l), chimeric galanin peptide C7 (m), galanin(2-29) (o), galanin(3-29) (Δ) and galanin (10-20) (s) produced Ki values of 1.2, 1.4, 14, >1,000 and >1,000 nM, respectively. The curves shown indicate the fits of the data points by nonlinear regression for one-site binding.

As shown in FIG. 2, compounds known to have galanin activity, i.e., galanin itself, galanin peptide C7 and galanin(2-29), were all competitive inhibitors of the labeled galanin, whereas the compounds lacking galanin activity, i.e., galanin (3-29) and galanin(10-20), were not. Thus, the assay has a high degree of ligand specificity and should be generally applicable to the identification of galanin agonists and antagonists.

Many modifications and variations of this invention can be made without departing from its spirit and scope, as will be apparent to those skilled in the art. The specific embodiments described herein are offered by way of example only, and the invention is to be limited only by the terms of the appended claims, together with the full scope of equivalents to which such claims are entitled.

We claim:

1. An isolated polypeptide comprising an amino acid sequence selected from the group consisting of SEQ ID NO: 2, SEQ ID NO: 4, and amino acids 57-424 of SEQ ID NO: 4.

2. The polypeptide of claim 1 comprising the amino acid sequence of SEQ ID NO: 2.

3. The polypeptide of claim 1 comprising the amino acid sequence of SEQ ID NO: 4.

4. The polypeptide of claim 1 comprising the amino acids 57-424 of SEQ ID NO: 4.

5. A complex comprising the polypeptide of claim 1 bound to an antibody.

6. The polypeptide of claim 2 comprising a modification selected from the group consisting of conjugation to an aliphatic ester, amidation of the polypeptide carboxyl terminus, amidation of an amino acid carboxyl side chains, O-acylated hydroxyl group-containing amino acid, N-acylated amino-terminus, N-acylated amino group containing amino acid, phosphorylation, sulfonation, biotinylation and glycosylation.

7. The polypeptide of claim 3 comprising a modification selected from the group consisting of conjugation to an aliphatic ester, amidation of the polypeptide carboxyl terminus, amidation of an amino acid carboxyl side chains, O-acylated hydroxyl group-containing amino acid, N-acylated amino-terminus, N-acylated amino group containing amino acid, phosphorylation, sulfonation, biotinylation and glycosylation.

8. The polypeptide of claim 4 comprising a modification selected from the group consisting of conjugation to an aliphatic ester, amidation of the polypeptide carboxyl terminus, amidation of an amino acid carboxyl side chains, O-acylated hydroxyl group-containing amino acid, N-acylated amino-terminus, N-acylated amino group containing amino acid, phosphorylation, sulfonation, biotinylation and glycosylation.

9. The polypeptide of claim 2 which is bound to galanin.

10. The polypeptide of claim 9 wherein the galanin is labeled with $^{125}I$.

11. The polypeptide of claim 3 which is bound to galanin.

12. The polypeptide of claim 11 wherein the galanin is labeled with $^{125}I$.

13. The polypeptide of claim 4 which is bound to galanin.

14. The polypeptide of claim 13 wherein the galanin is labeled with $^{125}I$.

15. A composition comprising the polypeptide of claim 2 and an adjuvant.

16. The composition of claim 15 wherein the adjuvant comprises a member selected from the group consisting of a water-in-oil emulsion containing peanut oil, Freund's complete adjuvant, Freund's incomplete adjuvant, a mineral gel, aluminum hydroxide, aluminum phosphate, alum, a surfactant, hexadecylamine, octadecylamine, lysolecithin, dimethyldioctadecylammonium bromide, N,N-dioctadecyl-N',N'-bis(2-hydroxymethyl) propanediamine, methoxyhexadecylglycerol, an ethylene oxide-propylene oxide polyol, a polyanion, pyran, dextran sulfate, poly IC, polyacrylic acid, carbopol, a peptide, muramyl dipeptide, dimethylglycine, tuftsin and an oil emulsion.

17. A composition comprising the polypeptide of claim 3 and an adjuvant.

18. The composition of claim 17 wherein the adjuvant comprises a member selected from the group consisting of a water-in-oil emulsion containing peanut oil, Freund's complete adjuvant, Freund's incomplete adjuvant, a mineral gel, aluminum hydroxide, aluminum phosphate, alum, a surfactant, hexadecylamine, octadecylamine, lysolecithin, dimethyldioctadecylammonium bromide, N,N-dioctadecyl-N',N'-bis(2-hydroxymethyl) propanediamine, methoxyhexadecylglycerol, an ethylene oxide-propylene oxide polyol, a polyanion, pyran, dextran sulfate, poly IC, polyacrylic acid, carbopol, a peptide, muramyl dipeptide, dimethylglycine, tuftsin and an oil emulsion.

19. A composition comprising the polypeptide of claim 4 and an adjuvant.

20. The composition of claim 19 wherein the adjuvant comprises a member selected from the group consisting of a water-in-oil emulsion containing peanut oil, Freund's complete adjuvant, Freund's incomplete adjuvant, a mineral gel, aluminum hydroxide, aluminum phosphate, alum, a surfactant, hexadecylamine, octadecylamine, lysolecithin, dimethyldioctadecylammonium bromide, N,N-dioctadecyl-N',N'-bis(2-hydroxymethyl) propanediamine, methoxyhexadecyiglycerol, an ethylene oxide-propylene oxide polyol, a polyanion, pyran, dextran sulfate, poly IC, polyacrylic acid, carbopol, a peptide, muramyl dipeptide, dimethylglycine, tuftsin and an oil emulsion.

* * * * *

SEQUENCE LISTING

```
<160>  22

<210>  1
<211>  1113
<212>  DNA
<213>  Rattus sp.
<220>
<221>  CDS
```

<222> (1)..(1113)

<400> 1

```
atg gct gac atc cag aac att tcg ctg gac agc cca ggg agc gta ggg      48
Met Ala Asp Ile Gln Asn Ile Ser Leu Asp Ser Pro Gly Ser Val Gly
1               5                   10                  15 gct gtg gca gtg cct gtg atc ttt gcc ctc atc ttc ctg ttg ggc atg      96
Ala Val Ala Val Pro Val Ile Phe Ala Leu Ile Phe Leu Leu Gly Met
            20                  25                  30 gtg ggc aat ggg ctg gtg ttg gct gtg cta ctg cag cct ggc cca agt     144
Val Gly Asn Gly Leu Val Leu Ala Val Leu Leu Gln Pro Gly Pro Ser
        35                  40                  45 gcc tgg cag gag caa ggg agt aca caa gat ctc ttc atc ctc aac ttg     192
Ala Trp Gln Glu Gln Gly Ser Thr Gln Asp Leu Phe Ile Leu Asn Leu
    50                  55                  60 gcc gtg gcc gac ctt tgc ttc atc ctg tgc tgc gtg ccc ttc cag gca     240
Ala Val Ala Asp Leu Cys Phe Ile Leu Cys Cys Val Pro Phe Gln Ala
65                  70                  75                  80 gcc atc tac acc ctg gat gcc tgg ctc ttt ggg gct ttc gtg tgc aag     288
Ala Ile Tyr Thr Leu Asp Ala Trp Leu Phe Gly Ala Phe Val Cys Lys
                85                  90                  95 acg gta cat ctg ctc atc tac ctc acc atg tat gcc agc agc ttc acc     336
Thr Val His Leu Leu Ile Tyr Leu Thr Met Tyr Ala Ser Ser Phe Thr
            100                 105                 110 ctg gcg gcc gtc tcc ctg gac agg tac ctg gct gtg cgg cac caa ctg     384
Leu Ala Ala Val Ser Leu Asp Arg Tyr Leu Ala Val Arg His Gln Leu
        115                 120                 125 cgc tcc aga gcc ctg cgc acc ccg tgc aac gcg cgc gcc gtg ggg         432
Arg Ser Arg Ala Leu Arg Thr Pro Cys Asn Ala Arg Ala Val Gly
    130                 135                 140 ctc gtg tgg ctg ctg ggg gct ctc ttt tcc gcg ccc tac cta agc tac     480
Leu Val Trp Leu Leu Gly Ala Leu Phe Ser Ala Pro Tyr Leu Ser Tyr
145                 150                 155                 160 tac ggc acg gtg cgc tac ggc gcg ctc gag ctc tgc gtg ccc gct ttg     528
Tyr Gly Thr Val Arg Tyr Gly Ala Leu Glu Leu Cys Val Pro Ala Leu
                165                 170                 175 gag gac gcg cgg cgg cgg cgc ttg gac gtg gcc gcc ttc gcc gcg ggc     576
Glu Asp Ala Arg Arg Arg Arg Leu Asp Val Ala Ala Phe Ala Ala Gly
            180                 185                 190 tac ctg ctg ccg gtg gcc gtg gtg agc ctg gcc tac gga cgc acg cta     624
Tyr Leu Leu Pro Val Ala Val Val Ser Leu Ala Tyr Gly Arg Thr Leu
        195                 200                 205 tgt ctt cta tgg gcc gcc gtg ggt ccc gcg ggc gcg gcg gca gag         672
Cys Leu Leu Trp Ala Ala Val Gly Pro Ala Gly Ala Ala Ala Glu
    210                 215                 220 gcg cgc aga cgg gcg acc ggc cgg gcg gga cgg gcc atg ctg gca gtg     720
Ala Arg Arg Arg Ala Thr Gly Arg Ala Gly Arg Ala Met Leu Ala Val
225                 230                 235                 240 gcc gcg ctc tac gcg ctt tgc tgg ggc ccg cac cac gcg ctc atc ctc     768
Ala Ala Leu Tyr Ala Leu Cys Trp Gly Pro His His Ala Leu Ile Leu
                245                 250                 255 tgc ttc tgg tac ggt cgg ttc gcc ttc agc ccg gcc acc tac gcc att     816
Cys Phe Trp Tyr Gly Arg Phe Ala Phe Ser Pro Ala Thr Tyr Ala Ile
            260                 265                 270 cgc ctg gcc tcg cac tgc ctc gcc tac gcc aac tcc tgc ctt aac ccg     864
Arg Leu Ala Ser His Cys Leu Ala Tyr Ala Asn Ser Cys Leu Asn Pro
        275                 280                 285 ctc gtc tac tcg ctc gcc tcg cgc cac ttc cgc gcg cgc ttc cgc cgc     912
Leu Val Tyr Ser Leu Ala Ser Arg His Phe Arg Ala Arg Phe Arg Arg
    290                 295                 300
```

-continued

| | | | | | | | | | | | | | | | |
|---|---|---|---|---|---|---|---|---|---|---|---|---|---|---|---|
| ctg | tgg | ccc | tgc | ggc | cgt | tgc | cgc | cac | cgc | cac | cac | cac | cgc | gct | cat | 960 |
| Leu | Trp | Pro | Cys | Gly | Arg | Cys | Arg | His | Arg | His | His | His | Arg | Ala | His | |
| 305 | | | | 310 | | | | | 315 | | | | | 320 | | |

| cga | gcc | ctc | cgt | cgt | gtc | cag | ccg | gcg | tct | tcg | ggc | ccc | gcc | ggt | tat | 1008 |
| Arg | Ala | Leu | Arg | Arg | Val | Gln | Pro | Ala | Ser | Ser | Gly | Pro | Ala | Gly | Tyr | |
| | | | 325 | | | | | 330 | | | | | 335 | | | |

| ccc | ggc | gac | gcc | agg | cct | cgt | ggt | tgg | agt | atg | gag | ccc | aga | ggg | gat | 1056 |
| Pro | Gly | Asp | Ala | Arg | Pro | Arg | Gly | Trp | Ser | Met | Glu | Pro | Arg | Gly | Asp | |
| 340 | | | | | 345 | | | | | 350 | | | | | | |

| gct | ctg | cgt | ggt | ggt | gga | gag | act | aga | cta | acc | ctg | tcc | ccc | agg | gga | 1104 |
| Ala | Leu | Arg | Gly | Gly | Gly | Glu | Thr | Arg | Leu | Thr | Leu | Ser | Pro | Arg | Gly | |
| | | 355 | | | | | 360 | | | | | 365 | | | | |

| cct | caa | taa | | | | | | | | | | | | | | 1113 |
| Pro | Gln | | | | | | | | | | | | | | | |
| | 370 | | | | | | | | | | | | | | | |

<210> 2
<211> 370
<212> PRT
<213> Rattus sp.

<400> 2

Met Ala Asp Ile Gln Asn Ile Ser Leu Asp Ser Pro Gly Ser Val Gly
1               5                   10                  15

Ala Val Ala Val Pro Val Ile Phe Ala Leu Ile Phe Leu Leu Gly Met
                20                  25                  30

Val Gly Asn Gly Leu Val Leu Ala Val Leu Leu Gln Pro Gly Pro Ser
            35                  40                  45

Ala Trp Gln Glu Gln Gly Ser Thr Gln Asp Leu Phe Ile Leu Asn Leu
        50                  55                  60

Ala Val Ala Asp Leu Cys Phe Ile Leu Cys Cys Val Pro Phe Gln Ala
65                  70                  75                  80

Ala Ile Tyr Thr Leu Asp Ala Trp Leu Phe Gly Ala Phe Val Cys Lys
                85                  90                  95

Thr Val His Leu Leu Ile Tyr Leu Thr Met Tyr Ala Ser Ser Phe Thr
                100                 105                 110

Leu Ala Ala Val Ser Leu Asp Arg Tyr Leu Ala Val Arg His Gln Leu
            115                 120                 125

Arg Ser Arg Ala Leu Arg Thr Pro Cys Asn Ala Arg Ala Ala Val Gly
        130                 135                 140

Leu Val Trp Leu Leu Gly Ala Leu Phe Ser Ala Pro Tyr Leu Ser Tyr
145                 150                 155                 160

Tyr Gly Thr Val Arg Tyr Gly Ala Leu Glu Leu Cys Val Pro Ala Leu
                165                 170                 175

Glu Asp Ala Arg Arg Arg Leu Asp Val Ala Ala Phe Ala Ala Gly
            180                 185                 190

Tyr Leu Leu Pro Val Ala Val Ser Leu Ala Tyr Gly Arg Thr Leu
        195                 200                 205

Cys Leu Leu Trp Ala Ala Val Gly Pro Ala Gly Ala Ala Ala Glu
210                 215                 220

Ala Arg Arg Arg Ala Thr Gly Arg Ala Gly Arg Ala Met Leu Ala Val
225                 230                 235                 240

Ala Ala Leu Tyr Ala Leu Cys Trp Gly Pro His His Ala Leu Ile Leu
                245                 250                 255

Cys Phe Trp Tyr Gly Arg Phe Ala Phe Ser Pro Ala Thr Tyr Ala Ile
            260                 265                 270

```
Arg Leu Ala Ser His Cys Leu Ala Tyr Ala Asn Ser Cys Leu Asn Pro
            275                 280                 285

Leu Val Tyr Ser Leu Ala Ser Arg His Phe Arg Ala Arg Phe Arg Arg
        290                 295                 300

Leu Trp Pro Cys Gly Arg Cys Arg His Arg His His Arg Ala His
305                 310                 315                 320

Arg Ala Leu Arg Arg Val Gln Pro Ala Ser Ser Gly Pro Ala Gly Tyr
                325                 330                 335

Pro Gly Asp Ala Arg Pro Arg Gly Trp Ser Met Glu Pro Arg Gly Asp
            340                 345                 350

Ala Leu Arg Gly Gly Gly Glu Thr Arg Leu Thr Leu Ser Pro Arg Gly
        355                 360                 365

Pro Gln
    370

<210>  3
<211>  1275
<212>  DNA
<213>  Homo sapiens
<220>
<221>  CDS
<222>  (1)..(1275)

<400>  3 atg act ttg gct ctg ctc tcc cct cct cca tct ccc acg agc ttc cag      48
Met Thr Leu Ala Leu Leu Ser Pro Pro Pro Ser Pro Thr Ser Phe Gln
1               5                  10                  15 ccc aga aca cct ggc cag acc cag gtc ggg gga gtt aga tcc cgg ggt      96
Pro Arg Thr Pro Gly Gln Thr Gln Val Gly Gly Val Arg Ser Arg Gly
            20                  25                  30 caa gca acc aga act ggg ggc tct tgc ctg agg att cca gct tct ctt     144
Gln Ala Thr Arg Thr Gly Gly Ser Cys Leu Arg Ile Pro Ala Ser Leu
        35                  40                  45 ccc agg tgc ccg tct gat ggg gag atg gct gat gcc cag aac att tca     192
Pro Arg Cys Pro Ser Asp Gly Glu Met Ala Asp Ala Gln Asn Ile Ser
    50                  55                  60 ctg gac agc cca ggg agt gtg ggg gcc gtg gca gtg cat gtg gtc ttt     240
Leu Asp Ser Pro Gly Ser Val Gly Ala Val Ala Val His Val Val Phe
65                  70                  75                  80 gcc cta atc ttc ctg ctg ggc aca gtg ggc aat ggg ctg gtg ctg gca     288
Ala Leu Ile Phe Leu Leu Gly Thr Val Gly Asn Gly Leu Val Leu Ala
                85                  90                  95 gtg ctc ctg cag cct ggc ccg agt gcc tgg cag gag cct tgc agc acc     336
Val Leu Leu Gln Pro Gly Pro Ser Ala Trp Gln Glu Pro Cys Ser Thr
            100                 105                 110 acg gac ctg ttc atc ctc aac ctg gcg gtg gct gac ctc tgc ttc atc     384
Thr Asp Leu Phe Ile Leu Asn Leu Ala Val Ala Asp Leu Cys Phe Ile
        115                 120                 125 ctg tgc tgc gtg ccc ttc caa gcc acc atc tac acg ctg gat gcc tgg     432
Leu Cys Cys Val Pro Phe Gln Ala Thr Ile Tyr Thr Leu Asp Ala Trp
    130                 135                 140 ctc ttt ggg gcc ctc gtc tgc aac gcc gtg cac ctc atc tac ctc         480
Leu Phe Gly Ala Leu Val Cys Asn Ala Val His Leu Ile Tyr Leu
145                 150                 155                 160 acc atg tac gcc agc agc ttt acg ctg gct gct gtc tcc gtg gac agg     528
Thr Met Tyr Ala Ser Ser Phe Thr Leu Ala Ala Val Ser Val Asp Arg
                165                 170                 175 tac ctg gcc gtg cgg cac ccg ctg cgc tcg cgc gcc ctg cgc acg ccg     576
Tyr Leu Ala Val Arg His Pro Leu Arg Ser Arg Ala Leu Arg Thr Pro
```

```
                180                 185                 190
cgt aac gcc cgc gcc gca gtg ggg ctg gtg tgg ctg ctg gcg gcg ctc         624
Arg Asn Ala Arg Ala Ala Val Gly Leu Val Trp Leu Leu Ala Ala Leu
        195                 200                 205 ttc tcg gcg ccc tac ctc agc tac tac ggc acc gtg cgc tac ggc gcg         672
Phe Ser Ala Pro Tyr Leu Ser Tyr Tyr Gly Thr Val Arg Tyr Gly Ala
210                 215                 220 ctg gag ctc tgc gtg ccc gcc tgg gag gac gcg cgc cgc gcc cgg             720
Leu Glu Leu Cys Val Pro Ala Trp Glu Asp Ala Arg Arg Ala Arg
225                 230                 235                 240 gac gtg gcc acc tac gct gcc ggc tac ctg ctg ccc gtg gcc gtg gtg         768
Asp Val Ala Thr Tyr Ala Ala Gly Tyr Leu Leu Pro Val Ala Val Val
                245                 250                 255 agc ctg gcc tac ggg cgc acg ctg cgc ttc ctg tgg gcc gcc gtg ggt         816
Ser Leu Ala Tyr Gly Arg Thr Leu Arg Phe Leu Trp Ala Ala Val Gly
            260                 265                 270 ccc gcg ggc gcg gcg gcg gcc gag gcg cgg cgg agg gcg acg ggc cgc         864
Pro Ala Gly Ala Ala Ala Ala Glu Ala Arg Arg Arg Ala Thr Gly Arg
        275                 280                 285 gcg ggg cgc gcc atg ctg gcg gtg gcc gcg ctc tac gcg ctc tgc tgg         912
Ala Gly Arg Ala Met Leu Ala Val Ala Ala Leu Tyr Ala Leu Cys Trp
    290                 295                 300 ggt ccg cac cac gcg ctc atc ctg tgc ttc tgg tac ggc cgc ttc gcc         960
Gly Pro His His Ala Leu Ile Leu Cys Phe Trp Tyr Gly Arg Phe Ala
305                 310                 315                 320 ttc agc ccg gcc acc tac gcc tgc cgc ctg gcc tca cac tgc ctg gcc         1008
Phe Ser Pro Ala Thr Tyr Ala Cys Arg Leu Ala Ser His Cys Leu Ala
                325                 330                 335 tac gcc aac tcc tgc ctc aac ccg ctc gtc tac gcg ctc gcc tcg cgc         1056
Tyr Ala Asn Ser Cys Leu Asn Pro Leu Val Tyr Ala Leu Ala Ser Arg
            340                 345                 350 cac ttc cgc gcg cgc ttc cgc cgc ctg tgg ccg tgc ggc cgc cga cgc         1104
His Phe Arg Ala Arg Phe Arg Arg Leu Trp Pro Cys Gly Arg Arg Arg
        355                 360                 365 cgc cac cgt gcc cgc cgc gct ttg cgt cgc gtc cgc ccc gcg tcc tcg         1152
Arg His Arg Ala Arg Arg Ala Leu Arg Arg Val Arg Pro Ala Ser Ser
    370                 375                 380 ggc cca ccc ggc tgc ccc gga gac gcc cgg cct agc ggg ggg ctg ctg         1200
Gly Pro Pro Gly Cys Pro Gly Asp Ala Arg Pro Ser Gly Gly Leu Leu
385                 390                 395                 400 gct ggt ggc ggc cag ggc ccg gag ccc agg gag gga ccc gtc cac ggc         1248
Ala Gly Gly Gly Gln Gly Pro Glu Pro Arg Glu Gly Pro Val His Gly
                405                 410                 415 gga gag gct gcc cga gga ccg gaa taa                                     1275
Gly Glu Ala Ala Arg Gly Pro Glu
                420

<210> 4
<211> 424
<212> PRT
<213> Homo sapiens

<400> 4

Met Thr Leu Ala Leu Leu Ser Pro Pro Ser Pro Thr Ser Phe Gln
1               5                   10                  15

Pro Arg Thr Pro Gly Gln Thr Gln Val Gly Val Arg Ser Arg Gly
            20                  25                  30

Gln Ala Thr Arg Thr Gly Gly Ser Cys Leu Arg Ile Pro Ala Ser Leu
        35                  40                  45
```

```
Pro Arg Cys Pro Ser Asp Gly Glu Met Ala Asp Ala Gln Asn Ile Ser
    50                  55                  60

Leu Asp Ser Pro Gly Ser Val Gly Ala Val Ala Val His Val Val Phe
65                  70                  75                  80

Ala Leu Ile Phe Leu Leu Gly Thr Val Gly Asn Gly Leu Val Leu Ala
                85                  90                  95

Val Leu Leu Gln Pro Gly Pro Ser Ala Trp Gln Glu Pro Cys Ser Thr
            100                 105                 110

Thr Asp Leu Phe Ile Leu Asn Leu Ala Val Ala Asp Leu Cys Phe Ile
        115                 120                 125

Leu Cys Cys Val Pro Phe Gln Ala Thr Ile Tyr Thr Leu Asp Ala Trp
    130                 135                 140

Leu Phe Gly Ala Leu Val Cys Asn Ala Val His Leu Leu Ile Tyr Leu
145                 150                 155                 160

Thr Met Tyr Ala Ser Ser Phe Thr Leu Ala Ala Val Ser Val Asp Arg
                165                 170                 175

Tyr Leu Ala Val Arg His Pro Leu Arg Ser Arg Ala Leu Arg Thr Pro
            180                 185                 190

Arg Asn Ala Arg Ala Ala Val Gly Leu Val Trp Leu Leu Ala Ala Leu
        195                 200                 205

Phe Ser Ala Pro Tyr Leu Ser Tyr Tyr Gly Thr Val Arg Tyr Gly Ala
    210                 215                 220

Leu Glu Leu Cys Val Pro Ala Trp Glu Asp Ala Arg Arg Arg Ala Arg
225                 230                 235                 240

Asp Val Ala Thr Tyr Ala Ala Gly Tyr Leu Leu Pro Val Ala Val Val
                245                 250                 255

Ser Leu Ala Tyr Gly Arg Thr Leu Arg Phe Leu Trp Ala Ala Val Gly
            260                 265                 270

Pro Ala Gly Ala Ala Ala Glu Ala Arg Arg Arg Ala Thr Gly Arg
        275                 280                 285

Ala Gly Arg Ala Met Leu Ala Val Ala Ala Leu Tyr Ala Leu Cys Trp
    290                 295                 300

Gly Pro His His Ala Leu Ile Leu Cys Phe Trp Tyr Gly Arg Phe Ala
305                 310                 315                 320

Phe Ser Pro Ala Thr Tyr Ala Cys Arg Leu Ala Ser His Cys Leu Ala
                325                 330                 335

Tyr Ala Asn Ser Cys Leu Asn Pro Leu Val Tyr Ala Leu Ala Ser Arg
            340                 345                 350

His Phe Arg Ala Arg Phe Arg Arg Leu Trp Pro Cys Gly Arg Arg Arg
        355                 360                 365

Arg His Arg Ala Arg Arg Ala Leu Arg Arg Val Arg Pro Ala Ser Ser
    370                 375                 380

Gly Pro Pro Gly Cys Pro Gly Asp Ala Arg Pro Ser Gly Gly Leu Leu
385                 390                 395                 400

Ala Gly Gly Gly Gln Gly Pro Glu Pro Arg Glu Gly Pro Val His Gly
                405                 410                 415

Gly Glu Ala Ala Arg Gly Pro Glu
            420

<210>  5
<211>  25
<212>  DNA
<213>  Artificial sequence
<220>
<223>  primer
```

-continued

<400> 5
gctggcagtg ctcctgcagc ctggc   25

<210> 6
<211> 27
<212> DNA
<213> Artificial sequence
<220>
<223> primer

<400> 6
aagcggccgt accagaagca caggatg   27

<210> 7
<211> 26
<212> DNA
<213> Artificial sequence
<220>
<223> primer

<400> 7
tgcgggcccc agcagagcgc gtagag   26

<210> 8
<211> 27
<212> DNA
<213> Artificial sequence
<220>
<223> primer

<400> 8
ccatcctaat acgactcact atagggc   27

<210> 9
<211> 24
<212> DNA
<213> Artificial sequence
<220>
<223> primer

<400> 9
catccagtgt gtagatggct gcct   24

<210> 10
<211> 23
<212> DNA
<213> Artificial sequence
<220>
<223> primer

<400> 10
actcactata gggctcgagc ggc   23

<210> 11
<211> 26
<212> DNA
<213> Artificial sequence
<220>
<223> primer

<400> 11
ccaagtgcct ggcaggagcc aagcag   26

<210> 12

```
<211>  28
<212>  DNA
<213>  Artificial sequence
<220>
<223>  primer

<400>  12 cgcgtagagc gcggccactg ccagcatg                                    28

<210>  13
<211>  26
<212>  DNA
<213>  Artificial sequence
<220>
<223>  primer
<220>
<221>  misc_feature
<222>  (16)..(16)
<223>  n is a, c, g, or t

<400>  13 caagggctga atcaanaagc tccagc                                      26

<210>  14
<211>  28
<212>  DNA
<213>  Artificial sequence
<220>
<223>  primer
<220>
<221>  misc_feature
<222>  (14)..(14)
<223>  n is a, c, g, or t

<400>  14 gcgggttaag gcangagttg gcgtaggc                                    28

<210>  15
<211>  25
<212>  DNA
<213>  Artificial sequence
<220>
<223>  primer

<400>  15 gtggtctttg ccctaatctt cctgc                                       25

<210>  16
<211>  25
<212>  DNA
<213>  Artificial sequence
<220>
<223>  primer

<400>  16 acggagacag cagccagcgt aaagc                                       25

<210>  17
<211>  25
<212>  DNA
<213>  Artificial sequence
<220>
<223>  primer

<400>  17 cttggaaggg cacgcagcac aggat                                       25
```

```
<210> 18
<211> 25
<212> DNA
<213> Artificial sequence
<220>
<223> primer

<400> 18
gccgcagagg tcagccaccg ccagg                                25

<210> 19
<211> 25
<212> DNA
<213> Artificial sequence
<220>
<223> primer

<400> 19
tgggcacagt gggcaatggg ctggt                                25

<210> 20
<211> 25
<212> DNA
<213> Artificial sequence
<220>
<223> primer

<400> 20
gaaactgagg aactctcacc ccttg                                25

<210> 21
<211> 25
<212> DNA
<213> Artificial sequence
<220>
<223> primer

<400> 21
ttgcaggcgg cagggtttat tccgg                                25

<210> 22
<211> 26
<212> DNA
<213> Artificial sequence
<220>
<223> primer

<400> 22
caagcaacca gaactggggg ctcttg                               26
```